(12) United States Patent
Uchida et al.

(10) Patent No.: US 9,107,657 B2
(45) Date of Patent: Aug. 18, 2015

(54) SUTURING AND LIGATING METHOD

(71) Applicant: Karl Storz GmbH & Co. KG, Tuttlingen (DE)

(72) Inventors: Kazunori Uchida, Hiroshima (JP); Tsuneyoshi Suzuki, Kanuma (JP); Hirofumi Mugishima, Kanuma (JP); Shinji Ishida, Fujinomiya (JP); Hiroaki Sano, Fujinomiya (JP)

(73) Assignee: KARL STORZ GMBH & CO. KG (DE)

( * ) Notice: Subject to any disclaimer, the term of this patent is extended or adjusted under 35 U.S.C. 154(b) by 119 days.

(21) Appl. No.: 13/661,822

(22) Filed: Oct. 26, 2012

(65) Prior Publication Data

US 2014/0121680 A1  May 1, 2014

(51) Int. Cl.
*A61B 17/04* (2006.01)
*A61B 17/062* (2006.01)
*A61B 17/29* (2006.01)

(52) U.S. Cl.
CPC ......... *A61B 17/0469* (2013.01); *A61B 17/0483* (2013.01); *A61B 17/062* (2013.01); *A61B 2017/2927* (2013.01)

(58) Field of Classification Search
CPC ............... A61B 17/0469; A61B 2017/0475; A61B 17/062
USPC ............... 606/139, 144, 145, 146, 147, 148; 112/475.17
See application file for complete search history.

(56) References Cited

U.S. PATENT DOCUMENTS

| 5,501,690 A * | 3/1996 | Measamer et al. ............ 606/146 |
| 2009/0240263 A1 | 9/2009 | Kawai et al. |
| 2009/0259105 A1 * | 10/2009 | Miyano et al. ................ 600/127 |

\* cited by examiner

*Primary Examiner* — Jonathan W Miles
(74) *Attorney, Agent, or Firm* — Whitmyer IP Group LLC

(57) ABSTRACT

A suturing and ligating method includes a needle piercing step of inserting a needle of a suture-needle assembly through a tissue in a body cavity, a needle gripping step of gripping the needle with a first gripper, a winding step of winding a suture strand of the suture-needle assembly in at least one turn around a first distal-end working unit by rolling the first distal-end working unit in at least one revolution, a transferring step of transferring the suture-needle assembly from the first gripper to a second gripper, a suture strand gripping step of gripping a portion of the suture strand that has not passed through the tissue, with the first gripper, a pulling step of pulling the first distal-end working unit out of a loop of the suture strand, and a tightening step of forming a knot of the suture strand.

2 Claims, 15 Drawing Sheets

SUTURING AND LIGATING METHOD

BACKGROUND OF THE INVENTION

1. Field of the Invention

The present invention relates to an intracoelomic suturing and ligating method for suturing and ligating a body tissue inside a body cavity of a living body using two manipulators.

2. Description of the Related Art

According to endoscopic surgery (also called laparoscopic surgery), it is customary to form a plurality of holes or incisions on the body surface of a patient, insert trocars (tubular instruments) respectively into the incisions to define forceps instrument passage ports, and introduce distal end portions of forceps instruments having shafts through the respective trocars into the body cavity of the patient for performing a surgical operation on the affected body part. End effectors such as a gripper for gripping a living tissue, scissors, an electrosurgical knife blade, etc., are mounted onto the distal end portions of the forceps instruments.

An endoscopic surgical operation performed by means of the forceps instruments requires a surgeon to be trained in advance, because a working space within the body cavity is small. Further, the forceps instruments need to be operated using the trocars as fulcrums. Since conventional forceps instruments that have heretofore been used do not have joints for making tilting movement on the distal end thereof, such forceps instruments tend to have a small degree of freedom, and the end effecter can be operated only on an extension of the shaft. Therefore, cases that can be handled in accordance with the usual training practice for endoscopic surgery are confined to a certain range. Moreover, a surgeon needs to be trained and have a considerably high level of skill in order to perform endoscopic surgery on other cases that do not fall within the limited range.

Attempts have been made to improve conventional forceps instruments, so as to develop a forceps instruments having a plurality of joints on the distal ends thereof (see, for example, U.S. Patent Application Publication No. 2009/0240263). Such a forceps instrument (or a manipulator) is free of the limitations and difficulties of conventional forceps instruments, can be operated easily, and can be applied to a wide variety of surgical cases. It is expected that the developed forceps instrument will be applied to surgical techniques that require intricate manipulative actions within small spaces, for example.

Endoscopic surgical operations involve a variety of surgical techniques. In particular, suturing and ligating are difficult to carry out in small spaces within body cavities, and should desirably be done easily. U.S. Patent Application Publication No. 2009/0240263, for example, has proposed a method of suturing and ligating a tissue in a body cavity using two manipulators each having a gripper opening and closing mechanism, a gripper rolling mechanism, and a gripper tilting mechanism. According to the proposed method, specifically, a surgeon operates one of the manipulators to grip a suture-needle assembly, and moves the distal end portion of the one manipulator along a circular path to wind the suture strand around the distal end portion of the other manipulator.

SUMMARY OF THE INVENTION

It is an object of the present invention to provide a suturing and ligating method which makes it easier to suture and ligate a tissue in a body cavity using manipulators even in a small space.

To achieve the above object, there is provided in accordance with the present invention a suturing and ligating method to be performed inside a body cavity using a first manipulator having a first distal-end working unit including a first gripper which is selectively openable and closable, the first distal-end working unit being capable of making a rolling movement, and a second manipulator having a second distal-end working unit including a second gripper which is selectively openable and closable, the first manipulator including a handle having a rolling operating unit, a shaft extending from the handle, a first distal-end working unit mounted on a distal end of the shaft, and a drive source mounted in the handle for rolling the first distal-end working unit, wherein the first distal-end working unit can be rolled in an unlimited angular range by the drive source which is energized when the rolling operating unit is operated, the method comprising a needle piercing step of inserting a needle of a suture-needle assembly through a tissue in the body cavity while leaving a portion of a suture strand of the suture-needle assembly uninserted in the tissue, a needle gripping step of gripping the needle with the first gripper, a winding step of winding the suture strand in at least one turn around the first distal-end working unit by rolling the first distal-end working unit in at least one revolution while gripping the needle with the first gripper, a transferring step of, after the winding step, transferring the suture-needle assembly from the first gripper to the second gripper, a suture strand gripping step of, after the transferring step, gripping a portion of the suture strand that has not passed through the tissue, with the first gripper, a pulling step of, after the suture strand gripping step, pulling the first distal-end working unit out of a loop of the suture strand wound around the first distal-end working unit, and a tightening step of, after the pulling step, forming a knot of the suture strand by moving the first distal-end working unit and the second distal-end working unit away from each other.

With the above suturing and ligating method according to the present invention, since the first distal-end working unit can be rolled in an unlimited angular range, the user can wind the suture strand easily in one turn or more around the first distal-end working unit by controlling the first gripper to make one revolution or more while gripping the needle with the first gripper. In thus winding the suture strand around the first distal-end working unit, the first manipulator only operates to roll the first distal-end working unit and does not move in the body cavity. Therefore, the user finds the first manipulator suitable for surgical techniques in a small space in the body cavity. Since, in the first manipulator, the user can roll the first distal-end working unit through an angular range of 360° or greater by the drive source simply by operating the rolling operating unit on the handle, the user can wind the suture strand around the first distal-end working unit reliably by a simple operation of the first manipulator. Consequently, the method according to the present embodiment can suture and ligate the tissue with more ease. The term "manipulator" used herein should be interpreted in a wide sense covering not only medical manipulators including a drive source and having a plurality of degrees of freedom on their distal end with an end effecter being actuatable about at least one axis by the driver source, but also general forceps which are free of a drive source and a plurality of axes.

In the above method, in the winding step, the first distal-end working unit may start to roll while the suture strand is displaced toward the first distal-end working unit by the second manipulator. The suture strand thus displaced toward the first distal-end working unit can be wound more easily around the first distal-end working unit. The user thus finds it easy and reliable to perform a surgical technique of winding the suture strand around the first distal-end working unit.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

An intracoelomic suturing and ligating method according to an embodiment of the present invention will be described below with reference to FIGS. 1 to 15. The intracoelomic suturing and ligating method according to the present embodiment is carried out using at least two manipulators. A medical manipulator for use in the intracoelomic suturing and ligating method according to the present embodiment will first be described below.

Figure 1:
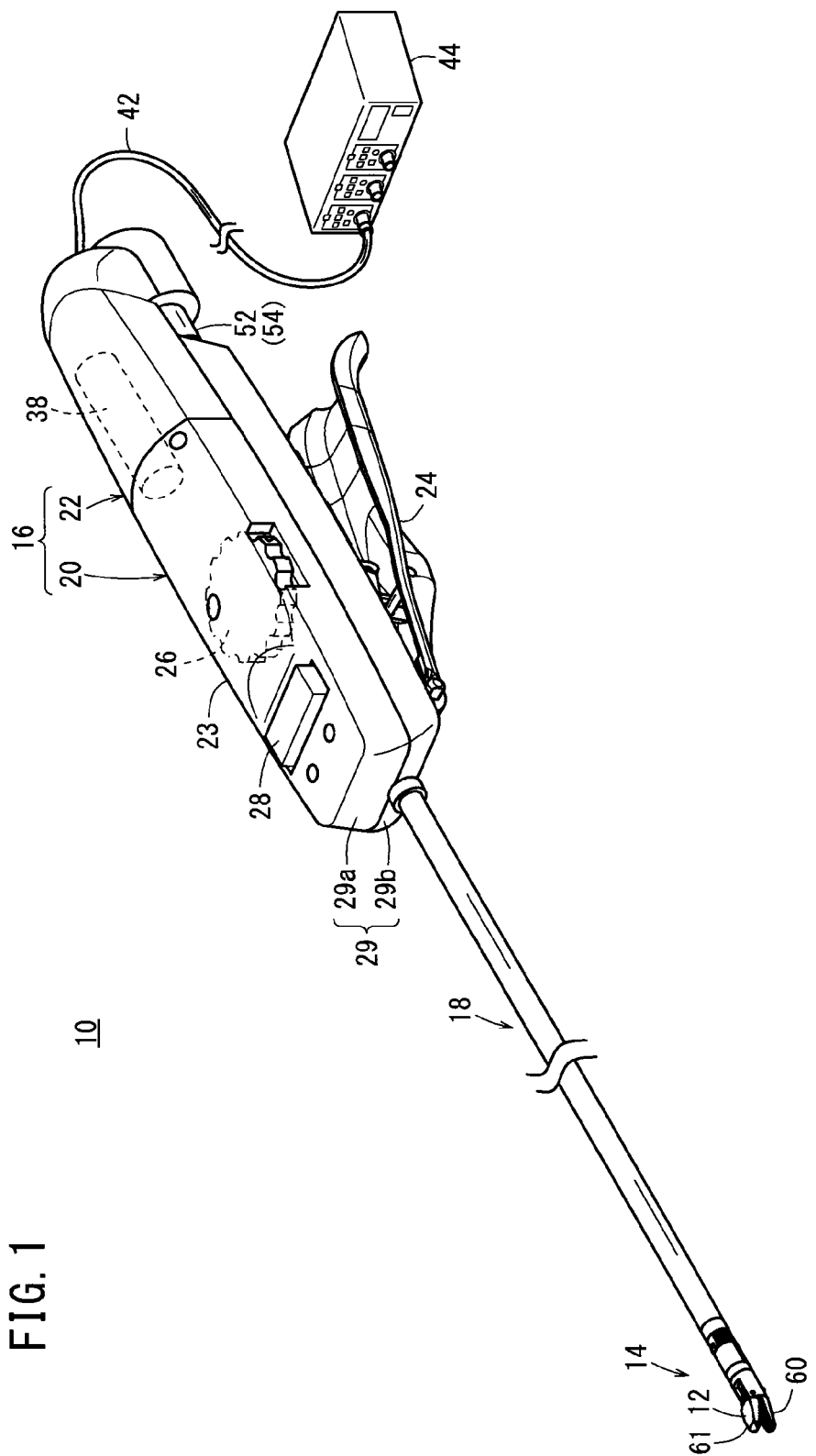
FIG. 1 is a perspective view, partly omitted from illustration, of a medical manipulator.

FIG. 1 is a perspective view, partly omitted from illustration, of a medical manipulator 10 (hereinafter referred to as "manipulator 10") according to the present embodiment. The manipulator 10 is a medical device having a gripper 12 on its distal end for gripping a needle, a suture strand, or a portion of a living body or touching a living body and treating the living body. The manipulator 10 is constructed as a needle driver for gripping a medical needle such as a curved needle or the like with the gripper 12 at a distal end thereof.

The manipulator 10 has a distal-end working unit 14 including the gripper 12, a handle 16 on a proximal end thereof for actuating the gripper 12, and a shaft 18 interconnecting the gripper 12 and the handle 16. The gripper 12, which serves as a mechanism for performing surgical treatments, includes a pair of first and second gripper members 60, 61 which can be opened and closed about an axis. The terms "distal end" and "proximal end" of the manipulator 10 are used herein to refer to the front and rear ends, respectively, of the manipulator 10.

The distal-end working unit 14 including the gripper 12 can change its posture with respect to the shaft 18 with a plurality of degrees of freedom. According to the present embodiment, the distal-end working unit 14 can be "tilted" (swung) to the left and right with respect to the longitudinal axis of the shaft 18 and can also be "rolled" about the longitudinal axis of the distal-end working unit 14. The distal-end working unit 14 may be tilted upwardly and downwardly, rather than leftwardly and rightwardly, with respect to the longitudinal axis of the shaft 18.

The shaft 18 is in the form of a long slender tubular member. The shaft 18 houses a plurality of members inserted and disposed therein which make up a power transmitting mechanism for transmitting mechanical power for opening/closing the gripper 12 and tilting and rolling the distal-end working unit 14 from the handle 16 to the distal-end working unit 14.

The handle 16 has a handle body 20 housing a plurality of operating units therein and a drive unit 22 including a motor 38. The drive unit 22 is removably mounted on the handle body 20. When the motor 38 of the drive unit 22 mounted on the handle body 20 is energized, drive power generated by the motor 38 is transmitted to the distal-end working unit 14. The handle body 20, the shaft 18, and the distal-end working unit 14 jointly make up a manipulator assembly of the manipulator 10. After the manipulator 10 has been used a predetermined number of times, the manipulator assembly may be removed from the drive unit 22 and discarded, and a new manipulator assembly may be connected to the drive unit 22. Therefore, the drive unit 22 can be used repeatedly in combination with a plurality of manipulator assemblies.

The handle body 20 includes a body section 23 connected to the proximal end of the shaft 18, a lever 24 (opening/closing operating unit) pivotally mounted on the body section 23, a tilting wheel 26 (tilting operating unit) housed in the body section 23, and a rolling switch 28 (rolling operating unit) mounted on the body section 23.

The body section 23, which serves as a grip to be gripped by a user when the user uses the manipulator 10, is shaped like a stick extending longitudinally along the axial directions of the shaft 18. The body section 23 has a casing 29 that comprises an upper cover 29a and a lower cover 29b. The casing 29 houses therein various drive components including pulleys, gears, wires, etc.

The lever 24 which opens and closes the gripper 12 is pivotally mounted on a lower portion of the body section 23 for vertical swinging movement about a distal end side portion thereof. According to the present embodiment, the lever 24 is constructed as a manual operating portion. When the user operates the lever 24, a manual operating force is mechanically transmitted from the lever 24 to the gripper 12 of the distal-end working unit 14, opening or closing the gripper 12. Specifically, when the user opens the lever 24, i.e., when the lever 24 is positioned away from the body section 23, the gripper 12 is opened, and when the user closes the lever 24, i.e., when the lever 24 is positioned close to the body section 23, the gripper 12 is closed.

The tilting wheel 26 which tilts the distal-end working unit 14 is disposed substantially centrally in the longitudinal directions of the body section 23. The tilting wheel 26 is also constructed as a manual operating portion, and has a circumferential edge partially exposed from the casing 29. When the user rotates the tilting wheel 26, a manual operating force applied thereto is mechanically transmitted through a tilting power transmitting system in the handle 16 and the shaft 18 to the distal-end working unit 14, tilting the distal-end working unit 14 into a direction not parallel to the axis of the shaft 18, i.e., into a leftward or right direction or an upward or downward direction.

The rolling switch 28 which rolls the distal-end working unit 14 is mounted on an upper portion of the body section 23 near its distal end. According to the present embodiment, the rolling switch 28 is constructed as an electric operating portion for applying an operation command to the motor 38 through a controller 44.

When the user presses the rolling switch 28, a signal depending on the position where the rolling switch 28 is pressed is electrically transmitted through a connector 54 and a cable 42 to the controller 44. Based on the transmitted signal, the controller 44 energizes the motor 38 to generate a rotary drive force, which is mechanically transmitted to the distal-end working unit 14, rotating the distal-end working unit 14 about the longitudinal axis thereof. According to the present embodiment, when the user presses a right region of the rolling switch 28, the distal-end working unit 14 rotates to the right, i.e., clockwise about the longitudinal axis as viewed from the user gripping the handle 16, and when the user presses a left region of the rolling switch 28, the distal-end working unit 14 rotates to the left, i.e., counterclockwise about the longitudinal axis as viewed from the user gripping the handle 16.

Figure 2:
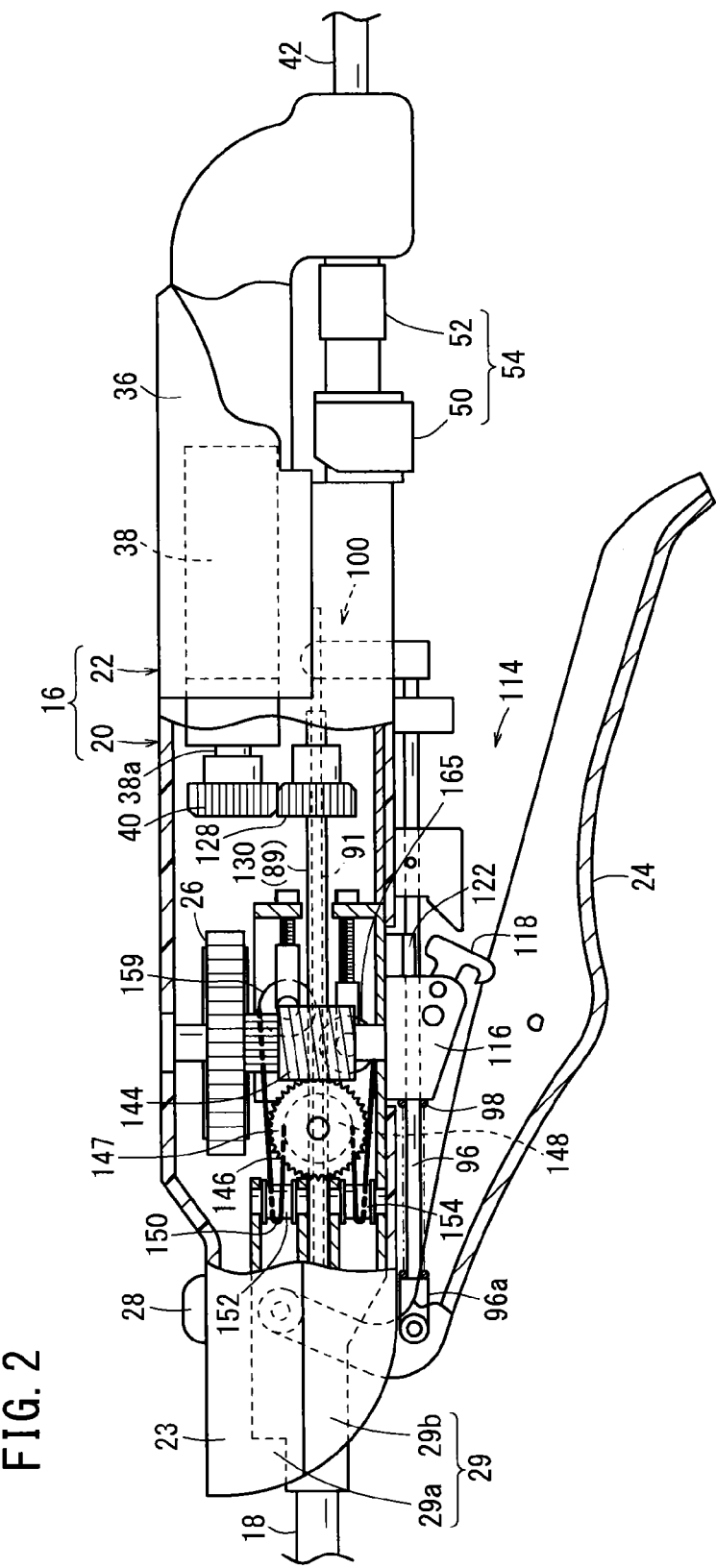
FIG. 2 is a side elevational view, partly in cross section, of a handle of the medical manipulator shown in FIG. 1.

As shown in FIG. 2, the drive unit 22 includes a housing 36, the motor 38 (drive source) which is disposed in the housing 36, and a drive gear 40 (pinion gear) fixed to an output shaft 38a of the motor 38. The drive unit 22 is removably mounted on a rear portion of the handle body 20. When the drive unit 22 is mounted on, i.e., connected to, the handle body 20, the housing 36 and the handle body 20 jointly make up the casing 29 of the handle 16. According to the present embodiment, the housing 36 is of an elongate shape extending in the longitudinal directions of the handle body 20. The drive gear 40 that is fixed to the output shaft 38a of the motor 38 projects into the handle body 20 from a distal end of the housing 36.

The drive unit 22 is electrically connected to the controller 44 by the cable 42 which includes a power line and a signal line. The controller 44 supplies electric power to the motor 38 and also performs drive control of the motor 38. The controller 44 receives electric power from an external power supply. When the user operates the rolling switch 28, a signal depending on the operation is sent to the controller 44, which controls drive of the motor 38.

When the drive unit 22 is mounted on the body section 23 of the handle body 20, the drive gear 40 fixed to the output shaft 38a of the motor 38 is brought into mesh with a driven gear 128 disposed in the body section 23. When the motor 38 is then energized, the rotary drive force generated by the motor 38 is transmitted through the drive gear 40 and the driven gear 128 to the handle body 20.

As shown in FIG. 2, the connector 54 includes a handle connector 50 mounted on a rear portion of the body section 23 of the handle body 20, and a unit connector 52 mounted on a rear portion of the drive unit 22. With the handle connector 50 and the unit connector 52 being connected to each other, when the rolling switch 28 is pressed, a signal generated by the rolling switch 28 is transmitted through the connector 54 and the signal line of the cable 42 to the controller 44, which energizes the motor 38 of the drive unit 22.

Figure 3:
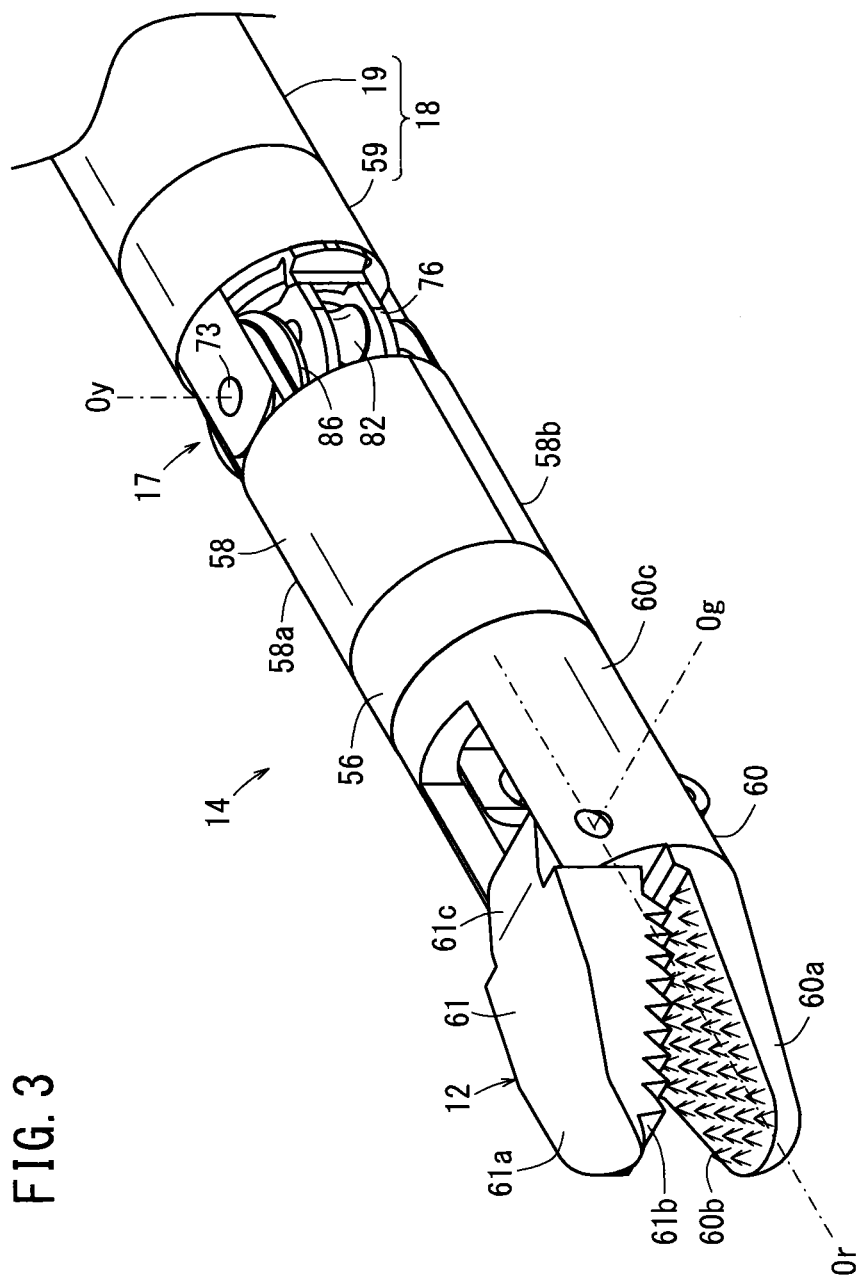
FIG. 3 is a perspective view of a distal-end working unit of the medical manipulator shown in FIG. 1.
Figure 4:
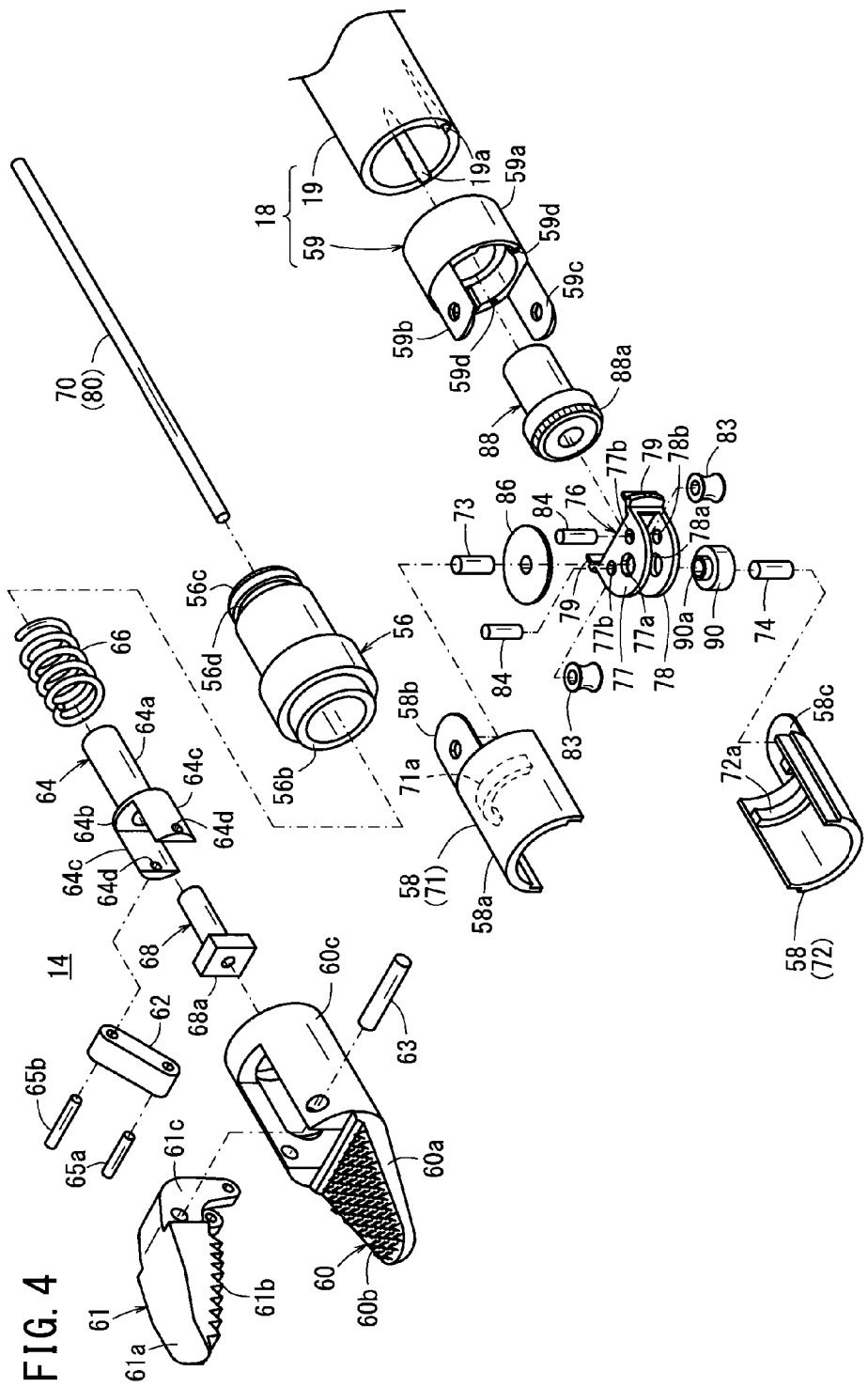
FIG. 4 is an exploded perspective view of the distal-end working unit shown in FIG. 3.
Figure 5:
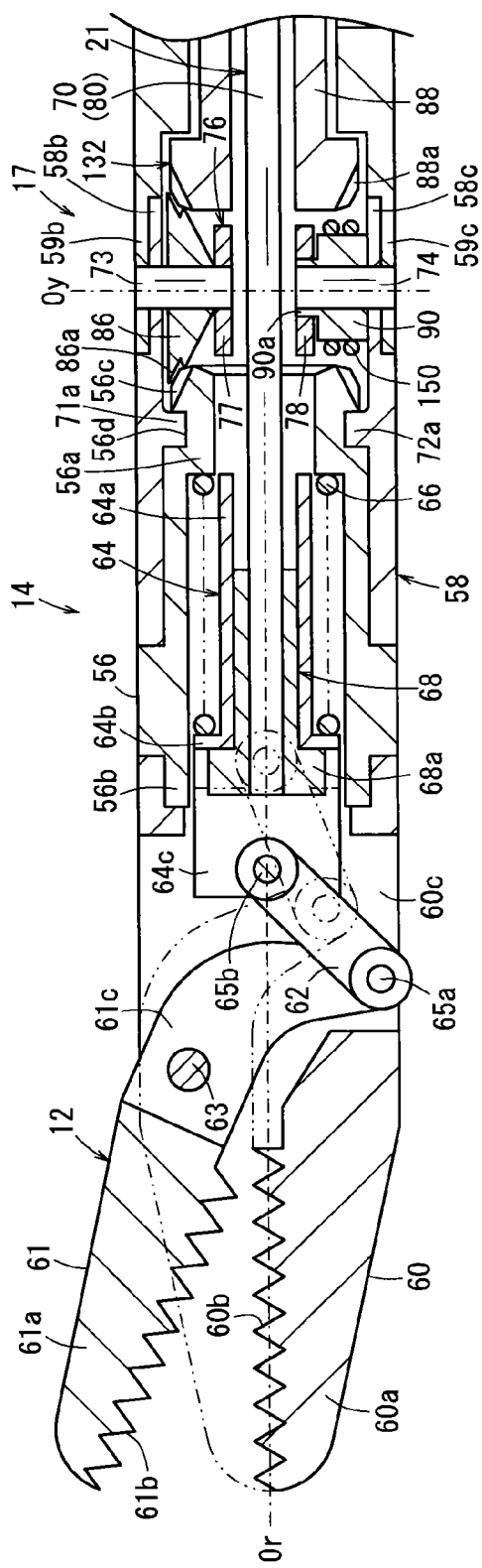
FIG. 5 is a vertical cross-sectional view of the distal-end working unit shown in FIG. 3.

FIG. 3 shows in perspective the distal-end working unit 14 which is coupled to the distal end of the shaft 18. FIG. 4 shows the distal-end working unit 14 in exploded perspective. FIG. 5 shows the distal-end working unit 14 in vertical cross section. As shown in FIGS. 3 to 5, the distal-end working unit 14 includes the gripper 12 which can be opened and closed, a hollow tubular rotary sleeve 56 (distal-end rotor) to which the gripper 12 is fixed, and a distal-end-side fulcrum block 58 (rotatable support tube) having an inner circumferential portion on which the rotary sleeve 56 is supported rotatably about its own axis.

The gripper 12 includes a first gripper member 60 and a second gripper member 61 which are rotatably coupled to each other by a pin 63, which extends transversely across the gripper 12, for rotating about a gripper axis Og aligned with the pin 63. The first gripper member 60 has a jaw 60a having a gripping surface 60b with a number of antislip protrusions. Similarly, the second gripper member 61 has a jaw 61a having a gripping surface 61b with a number of antislip protrusions. The first gripper member 60 has a proximal portion 60c having a substantially hollow cylindrical shape, and the second gripper member 61 has a proximal portion 61c rotatably coupled to the proximal portion 60c by the pin 63. The gripping surface 60b of the first gripper member 60 and the gripping surface 61b of the second gripper member 61 serve to jointly grip an object to be gripped such as a needle or the like.

The proximal portion 61c of the second gripper member 61 is coupled to a transmitting member 64 by a link member 62. The proximal portion 61c and the link member 62, and the link member 62 and the transmitting member 64 are rotatably coupled to each other by pins 65a, 65b, respectively. The transmitting member 64 has a guide tube 64a, a flange 64b disposed on a distal end of the guide tube 64a, and a pair of parallel support arms 64c extending from edges of the flange 64b toward the distal end. The transmitting member 64 is axially movably disposed in the rotary sleeve 56. The pin 65b is fitted in pin holes 64d formed respectively in the support arms 64c.

A compression spring 66 is disposed between the transmitting member 64 and the rotary sleeve 56. The compression spring 66 has an end which abuts against the flange 64b of the transmitting member 64 and another end which abuts against a step 56a on the inner circumferential portion of the rotary sleeve 56. The compression spring 66 normally biases the transmitting member 64 resiliently toward the distal end.

An end collar 68 is inserted into the transmitting member 64 from the distal end side thereof through a space between the support arms 64c. The end collar 68 has an engaging flange 68a on its distal end, which abuts against and engages the distal end surface of the guide tube 64a of the transmitting member 64. The end collar 68 is fixed to the distal end of a pull wire 70 which extends through a joint 17 (see FIGS. 5 and 6) between the distal-end working unit 14 and the shaft 18.

The pull wire 70 is a member that is movable back and forth in the shaft 18 and the distal-end working unit 14 in response to the user's action on the lever 24 of the handle 16. When the pull wire 70 is longitudinally displaced toward the proximal end, the end collar 68, which is fixed to the pull wire 70, pushes the transmitting member 64 toward the proximal end. The transmitting member 64 is thus displaced toward the proximal end against the biasing force of the compression spring 66. As the transmitting member 64 is displaced toward the proximal end, it pulls the link member 62 to cause the second gripper member 61 to turn toward the first gripper member 60 about the pin 63, so that the gripper 12 is closed. In FIG. 5, the imaginary lines indicate the second gripper member 61 that is moved to a position where the gripping surface 61b of the second gripper member 61 and the gripping surface 60b of the first gripper member 60 contact each other so as to bring the gripper 12 into a closed state.

When the pull wire 70 and the end collar 68 are displaced toward the distal end from the closed state in which the gripping surface 61b of the second gripper member 61 and the gripping surface 60b of the first gripper member 60 have contacted each other, the transmitting member 64 is also displaced toward the distal end under the resilient force of the compression spring 66. The transmitting member 64 pushes the link member 62 to cause the second gripper member 61 to turn away from the first gripper member 60 about the pin 63, so that the gripper 12 is opened. In FIG. 5, the solid lines indicate the second gripper member 61 that is moved to a position where the gripping surface 61b of the second gripper member 61 and the gripping surface 60b of the first gripper member 60 are fully out of contact each other so as to bring the gripper 12 into an open state. In this manner, the gripper 12 opens and closes.

In the present embodiment, the first gripper member 60 is constructed as a fixed gripper member and the second gripper member 61 as a movable gripper member. However, both the first gripper member 60 and the second gripper member 61 may be constructed as movable gripper members.

The rotary sleeve 56 has a reduced-diameter distal end portion 56b securely fitted in the proximal portion 60c of the first gripper member 60. The rotary sleeve 56 also has a bevel gear 56c on its proximal end and an annular groove 56d formed in an outer circumferential surface thereof at a position closer to the distal end thereof than the bevel gear 56c. The gripper 12, the rotary sleeve 56, the transmitting member 64, the end collar 68, and the compression spring 66 are rotatable integrally with respect to the distal-end-side fulcrum block 58 about a roll axis Or aligned with the longitudinal axis of the distal-end working unit 14.

The distal-end-side fulcrum block 58 is capable of changing its posture with respect to the axis of the shaft 18. The rotary sleeve 56 is rotatably supported by the inner circumferential portion of the distal-end-side fulcrum block 58. The distal-end-side fulcrum block 58 includes a semicylindrical upper block member 71 and a semicylindrical lower block member 72, which are combined with each other into a hollow cylindrical assembly as the distal-end-side fulcrum block 58.

The upper block member 71 and the lower block member 72 have respective arcuate ridges 71a, 72a on respective inner circumferential portions thereof. The arcuate ridges 71a, 72a slidably engage in the annular groove 56d of the rotary sleeve 56, so that the rotary sleeve 56 is rotatable, but axially immovable, with respect to the distal-end-side fulcrum block 58.

The distal-end-side fulcrum block 58 is coupled to a shaft-side fulcrum block 59 by upper and lower joint pins 73, 74 so as to rotate about a tilting axis Oy. The shaft-side fulcrum block 59 is fixed to the distal end of a hollow shaft body 19 which serves as a body section of the shaft 18. The shaft-side fulcrum block 59 and the shaft body 19 jointly make up the shaft 18.

The tilting axis Oy extends vertically. However, the tilting axis Oy may extend along any one of directions to intersect with the axis of the shaft body 19. The distal-end-side fulcrum block 58 has a tubular member 58a including the upper block member 71 and the lower block member 72, and a pair of parallel tongue pieces 58b, 58c projecting toward the proximal end from respective upper and lower portions of the proximal end of the tubular member 58a. The shaft-side fulcrum block 59 has a tubular member 59a and a pair of parallel tongue pieces 59b, 59c projecting toward the distal end from respective upper and lower portions of the distal end of the tubular member 59a. The joint pins 73, 74 are fitted in respective holes formed in the tongue pieces 58b, 58c of the distal-end-side fulcrum block 58 and the tongue pieces 59b, 59c of the shaft-side fulcrum block 59.

Figure 6:
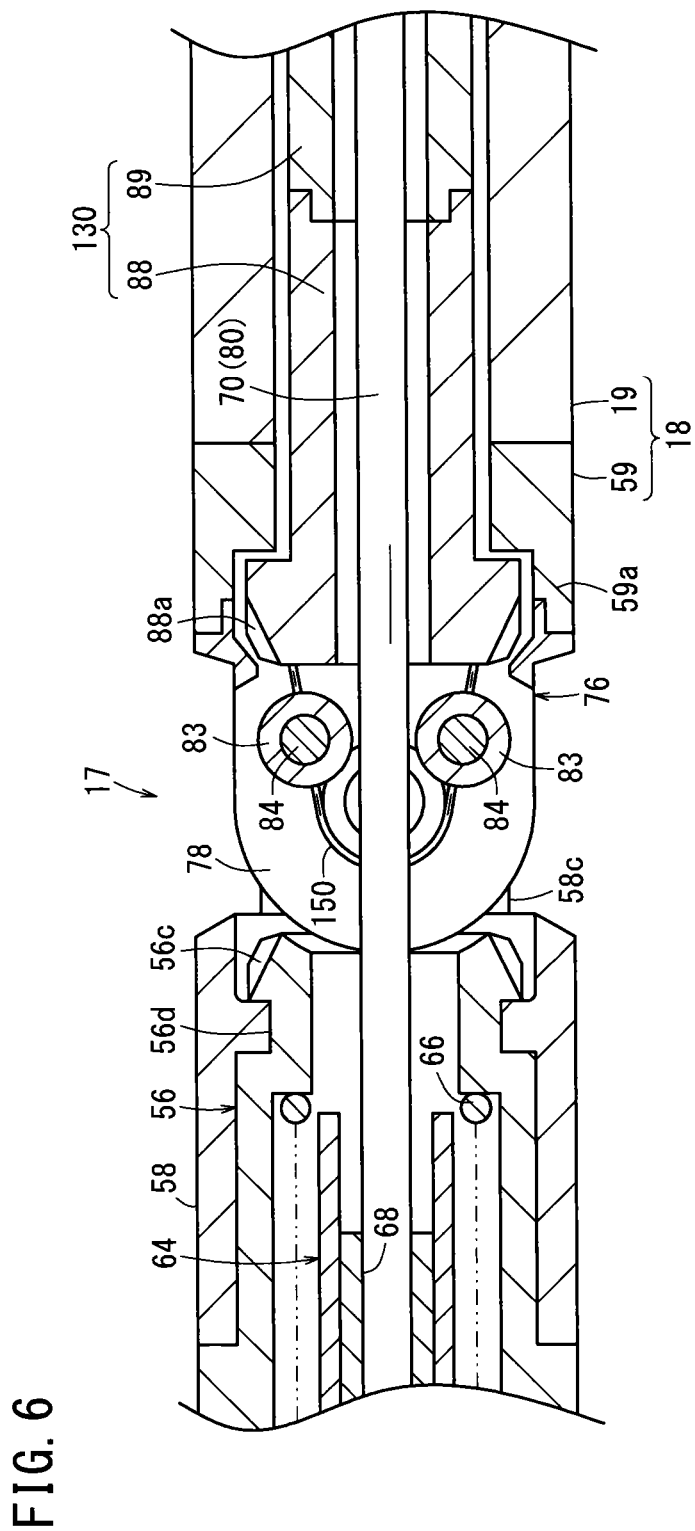
FIG. 6 is a vertical cross-sectional view of a joint and its peripheral regions with the distal-end working unit aligned with a shaft of the medical manipulator.

As shown in FIGS. 4 to 6, the joint 17 includes a support block 76 that is mounted on the distal end of the tubular member 59a of the shaft-side fulcrum block 59. The support block 76 has a pair of parallel upper and lower support plates 77, 78 which face each other and a pair of connectors 79 interconnecting left and right rear end portions of the support plates 77, 78. The upper support plate 77 has a central pin hole 77a formed therein in which the upper joint pin 73 is inserted, and a pair of left and right pin holes 77b formed therein in which upper ends of two pins 84 are inserted respectively. The lower support plate 78 has a central hole 78a formed therein in which a reduced-diameter upper end portion 90a of a driven pulley 90 is inserted, and a pair of left and right pin holes 78b formed therein in which lower ends of the two pins 84 are inserted respectively.

Two guide rollers 83 for guiding the pull wire 70 are disposed respectively on both sides of the pull wire 70 in the joint 17 near the tilting axis Oy about which the distal-end working unit 14 is tiltable with respect to the shaft 18. The guide rollers 83 are disposed between the upper and lower support plates 77, 78 and rotatably supported on the respective pins 84 which extend parallel to each other and are spaced from each other. The pull wire 70 extends through a gap between the guide rollers 83.

As shown in FIG. 5, the joint 17 between the distal-end working unit 14 and the shaft 18 includes the upper and lower joint pins 73, 74 aligned with the tilting axis Oy. The pull wire 70, which serves as part of a gripper opening and closing drive force transmitter 80, is movable back and forth through a gap between the joint pins 73, 74 in directions perpendicular to the axes of the joint pins 73, 74.

A bevel gear 86 (intermediate member) is rotatably supported by the upper joint pin 73 between the upper support plate 77 and the tongue piece 58b of the distal-end-side fulcrum block 58. The bevel gear 86 is rotatable independently of the upper support plate 77 and the tongue piece 58b. The bevel gear 86 has gear teeth 86a which mesh with the bevel gear 56c on the proximal end of the rotary sleeve 56 and also mesh with a bevel gear 88a on the distal end of a gear sleeve 88. The gear sleeve 88 is in the form of a hollow cylindrical member having the bevel gear 88a, and through which the pull wire 70 is inserted.

When the gear sleeve 88 is rotated about its own axis, a rotary drive force is transmitted from the gear sleeve 88 through the bevel gear 86 and the bevel gear 56c to the rotary sleeve 56. The rotary sleeve 56 and the gripper 12 coupled thereto are now rotated with respect to the distal-end-side fulcrum block 58 about the roll axis Or. This rotation is referred to as a rolling movement of the distal-end working unit 14.

The driven pulley 90 is rotatably supported by the lower joint pin 74 between the lower support plate 78 and the tongue piece 58c of the distal-end-side fulcrum block 58. The driven pulley 90 is fixed to an inner surface of the tongue piece 58c. The driven pulley 90 and the distal-end-side fulcrum block 58 are thus swingable together with respect to the shaft-side fulcrum block 59. A tilting wire 150 is wound around the driven pulley 90. The tilting wire 150 has a portion fixed to the driven pulley 90 and extends through the shaft 18 to the handle 16.

When the driven pulley 90 is rotated about its own axis by the tilting wire 150, the distal-end-side fulcrum block 58 that is fixed to the driven pulley 90 is rotated in unison with the driven pulley 90. The distal-end working unit 14 which includes the distal-end-side fulcrum block 58, the rotary sleeve 56, and the gripper 12 is now rotated with respect to the shaft 18 about the tilting axis Oy. This movement is referred to as a tilting movement of the distal-end working unit 14.

The distal-end working unit 14 can make a tilting movement in a range of certain areas on both a positive side (right side) and a negative side (left side) of a central position (reference position) at which the distal-end working unit 14 is aligned with the shaft 18. According to the present embodiment, the tilting movement range of the distal-end working unit 14 is of from +70° to −70°.

Figure 7:
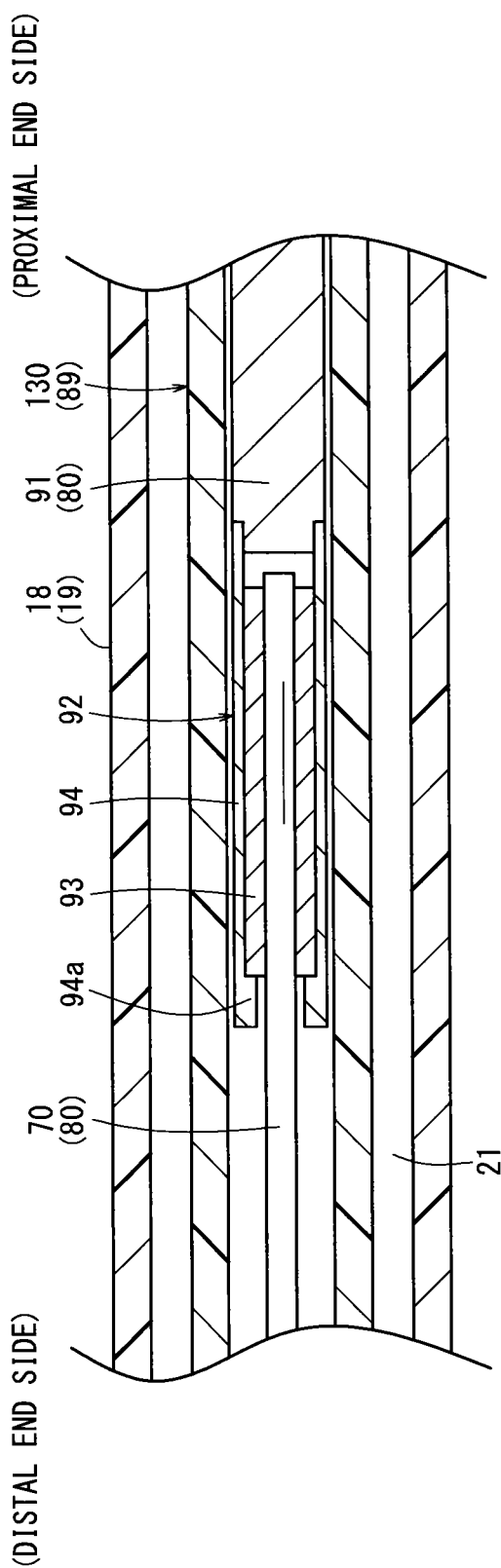
FIG. 7 is a vertical cross-sectional view of a joining structure by which a pull wire and a pull rod are joined to each other and its peripheral region.

FIG. 7 shows in vertical cross section a joining structure 92 by which the pull wire 70 and a pull rod 91 are joined to each other and its peripheral region. As shown in FIG. 7, the pull wire 70 and the pull rod 91, which jointly make up the gripper opening and closing drive force transmitter 80, are rotatable relatively to each other in a hollow shaft 89 that is coupled to the proximal end of the gear sleeve 88. The pull wire 70 and the pull rod 91 are joined to each other such that a pulling force applied to the pull rod 91 in a direction toward its proximal end will be transmitted to the pull wire 70. Specifically, a wire collar 93 is fixed to the proximal end of the pull wire 70, and a hollow outer collar 94 is fixed to the distal end of the pull rod 91. The wire collar 93 is disposed in the outer collar 94. The wire collar 93 is rotatable about its own axis within the outer collar 94, but is prevented from being pulled out of the outer collar 94 by a reduced-diameter portion 94a on the distal end of the outer collar 94 engaging with the wire collar 93.

Since the manipulator is thus constructed, when the pull rod 91 is displaced axially, the pull wire 70 that is joined to the pull rod 91 by the joining structure 92 is also displaced axially, opening or closing the gripper 12. When the distal-end working unit 14 is rolled about the roll axis Or, the pull wire 70 rotates with respect to the pull rod 91. Therefore, the joining structure 92 does not present an obstacle to the rolling movement of the distal-end working unit 14.

As shown in FIG. 2, the pull rod 91 extends through the hollow shaft 89 and has its proximal end projecting from the proximal end of the hollow shaft 89. The lever 24 has a distal end swingably coupled to the body section 23 near the distal end thereof. A lever rod 96 has a distal end pivotally connected to the lever 24 near its distal end. The lever rod 96 is disposed beneath the body section 23 substantially parallel to a longitudinal axis of the body section 23.

A hook holder 116 which supports a hook member 118 thereon is fixed to a lower portion of the body section 23. A compression spring 98 is disposed around the lever rod 96 between a distal end surface of the hook holder 116 and an increased-diameter portion 96a on the distal end of the lever rod 96. The compression spring 98 normally biases the lever rod 96 resiliently toward its distal end. The lever 24 that is coupled to the lever rod 96 is subject at all times to a force from the compression spring 98 in a direction to displace the lever 24 away from the body section 23 by resilient force of the compression spring 98. A drive force applied from the lever 24 is transmitted through an intermediate transmitting mechanism 100 to the gripper opening and closing drive force transmitter 80.

The position at which the lever 24 is open from, i.e., displaced away from, the body section 23 (see FIG. 2) is referred as an initial position. In the initial position, the pull rod 91 is axially displaced forwardly to a position where the gripper 12 is fully opened. When the user grips the lever 24 and pulls the lever 24 toward the body section 23, i.e., closes the lever 24, the lever rod 96 is displaced rearwardly toward the proximal end. At this time, the pull rod 91 is pulled rearwardly toward the proximal end by the intermediate transmitting mechanism 100, closing the gripper 12.

A mechanism for enabling the distal-end working unit 14 to make a rolling movement will be described below mainly with reference to FIGS. 2 and 5. According to the present embodiment, the distal-end working unit 14 makes a rolling movement when the drive force from the motor 38 is transmitted to the distal-end working unit 14. A rolling drive mechanism for rolling the distal-end working unit 14 includes the motor 38, the drive gear 40 fixed to the output shaft 38a of the motor 38, the driven gear 128 which meshes with the drive gear 40, the hollow shaft 89 to which the driven gear 128 is fixed, the gear sleeve 88 joined to the distal end of the hollow shaft 89, the bevel gear 86 which meshes with the bevel gear 88a of the gear sleeve 88, and the rotary sleeve 56 having the bevel gear 56c which meshes with the bevel gear 86. The gear sleeve 88 and the hollow shaft 89, which have respective ends facing and joined to each other in the hollow shaft body 19, jointly make up a rolling motion transmitting tube 130. The rolling motion transmitting tube 130, the bevel gear 86, and the rotary sleeve 56 jointly make up a rotary motion transmitter 132 for transmitting a rotary drive force from the handle 16 to the distal-end working unit 14.

With the drive unit 22 mounted on the handle body 20 and the controller 44 electrically connected to the power supply, when the user who is gripping the handle 16 presses the rolling switch 28 shown in FIG. 1, etc., the motor 38 is energized, generating a rotary drive force, which is transmitted through the drive gear 40, the driven gear 128, the rolling motion transmitting tube 130, the bevel gear 86, and the rotary sleeve 56 to the distal-end working unit 14, thereby rolling the distal-end working unit 14 about the roll axis Or.

The manipulator 10 transmits the rotary drive force from the handle 16 to the distal-end working unit 14 mainly through the rolling motion transmitting tube 130, rather than wires and pulleys. Therefore, the distal-end working unit 14 can be rolled in an unlimited angular range. Since the gripper opening and closing drive force transmitter 80, i.e., the pull wire 70 and the pull rod 91, is inserted and disposed in the rolling motion transmitting tube 130, the gripper opening and closing drive force transmitter 80 can transmit the drive force to the gripper 12 without being affected by rotation of the rolling motion transmitting tube 130.

As shown in FIG. 5, in the gripper opening and closing drive force transmitter 80, a portion corresponding to the joint 17 (i.e., the pull wire 70) is flexible. Therefore, the gripper opening and closing drive force transmitter 80 can transmit the drive force to the gripper 12 through a simple structure. The distal-end working unit 14 is thus of a relatively simple mechanism for opening/closing and also tilting the distal-end working unit 14 and also for rolling the distal-end working unit 14 in an unlimited angular range.

A mechanism for enabling the distal-end working unit 14 to make a tilting movement will be described below. As shown in FIG. 2, the handle body 20 houses therein a worm gear 144 rotatable about a vertical axis in response to rotation of the tilting wheel 26 and a rotor assembly 146 rotatable about a transversely horizontal axis of the body section 23 and having a worm wheel 147 which meshes with the worm gear 144.

The rotor assembly 146 also has a drive pulley 148 coaxially joined to the worm wheel 147 for rotation in unison therewith. The tilting wire 150 is wound around the drive pulley 148, extends through the shaft 18 toward the distal end, and is wound around the driven pulley 90 at a distal end portion of the shaft 18 (see FIG. 5 etc.). The tilting wire 150 is also wound around a first intermediate pulley 152 and a second intermediate pulley 154 that are disposed in the handle body 20 forwardly of the drive pulley 148, and around a first tension pulley 159 and a second tension pulley 165 that are disposed in the handle body 20 rearwardly of the drive pulley 148.

The shaft 18 and the rolling motion transmitting tube 130 define an annular space therebetween which extends axially through the shaft 18. The tilting wire 150 is inserted in the annular space. As shown in FIG. 4, axial holes 59*d* are formed in the shaft-side fulcrum block 59 and axial grooves 19*a* are formed in the inner wall of the hollow shaft body 19. The tilting wire 150 that is wound around the driven pulley 90 (see FIG. 5) extends through the axial holes 59*d* and the axial grooves 19*a* into the shaft 18.

When the user manually turns the tilting wheel 26 shown in FIGS. 1 and 2, the force applied to the tilting wheel 26 is transmitted from the worm gear 144 to the rotor assembly 146, moving the tilting wire 150 wound around the drive pulley 148 of the rotor assembly 146. The movement of the tilting wire 150 is transmitted through the shaft 18 to the driven pulley 90, which is rotated to tilt the distal-end working unit 14 with respect to the shaft 18.

In the present embodiment, the distal-end working unit 14 is electrically rolled by the motor 38, and manually tilted and opened/closed by the user. However, the manipulator 10 may be modified such that the distal-end working unit 14 is also electrically tilted and/or electrically opened/closed.

An intracoelomic suturing and ligating method according to the present embodiment will be described in detail below with reference to FIGS. 8 to 15. The intracoelomic suturing and ligating method is performed by the user using two manipulators 10. For illustrative purposes, these two manipulators 10 will be referred to as a first manipulator 10*a* and a second manipulator 10*b*. The distal-end working unit 14 and the gripper 12 of the first manipulator 10*a* will be referred to as a first distal-end working unit 14*a* and a first gripper 12*a*, and the distal-end working unit 14 and the gripper 12 of the second manipulator 10*b* will be referred to as a second distal-end working unit 14*b* and a second gripper 12*b*.

It is assumed that in FIGS. 8 to 15, the first manipulator 10*a* is positioned on the right-hand side so as to be handled by the right hand of the user, typically a surgeon, and the second manipulator 10*b* is positioned on the left-hand side so as to be handled by the left hand of the user. The first manipulator 10*a* may be positioned so as to be handled by the dominant hand of the user.

The user carries out the intracoelomic suturing and ligating method in an endoscopic surgical operation on a patient, for example, while viewing images acquired from an endoscope, not shown, inserted into a body cavity of the patient after the user has inserted the distal end portions of the first manipulator 10*a* and the second manipulator 10*b* through respective trocars into the body cavity and has performed certain preparatory actions and surgical techniques on the patient.

Figure 14:
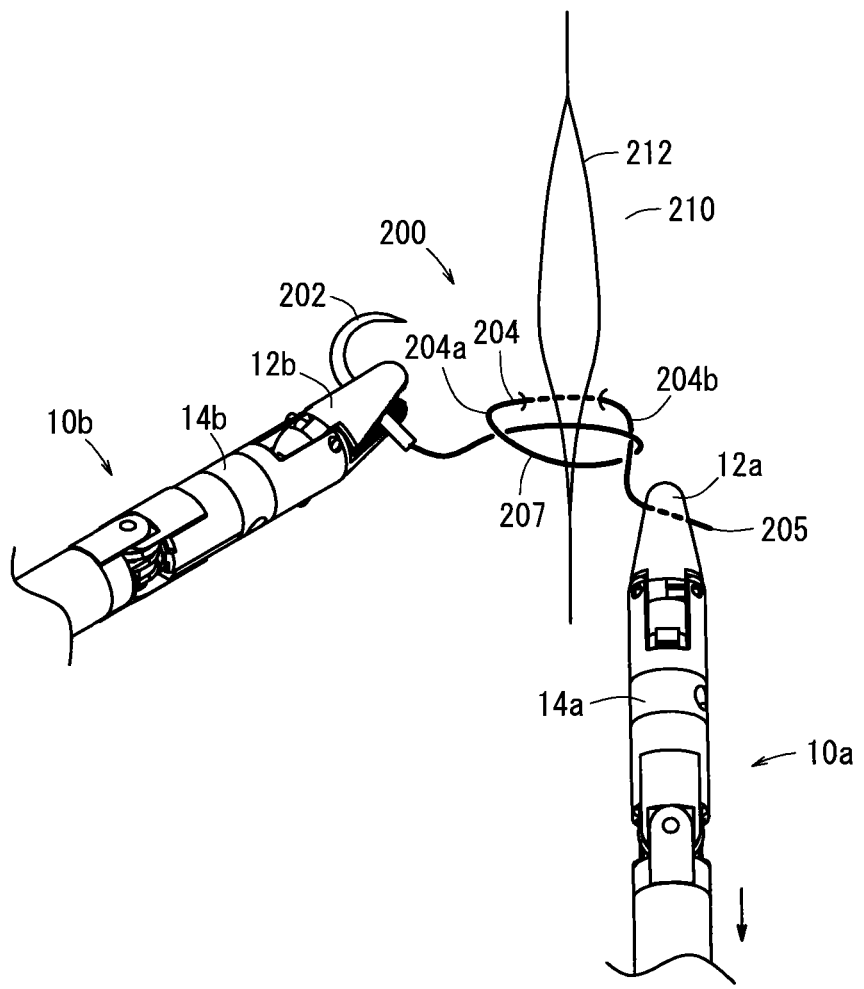
FIG. 14 is a seventh view illustrative of the intracoelomic ligating method.
Figure 15:
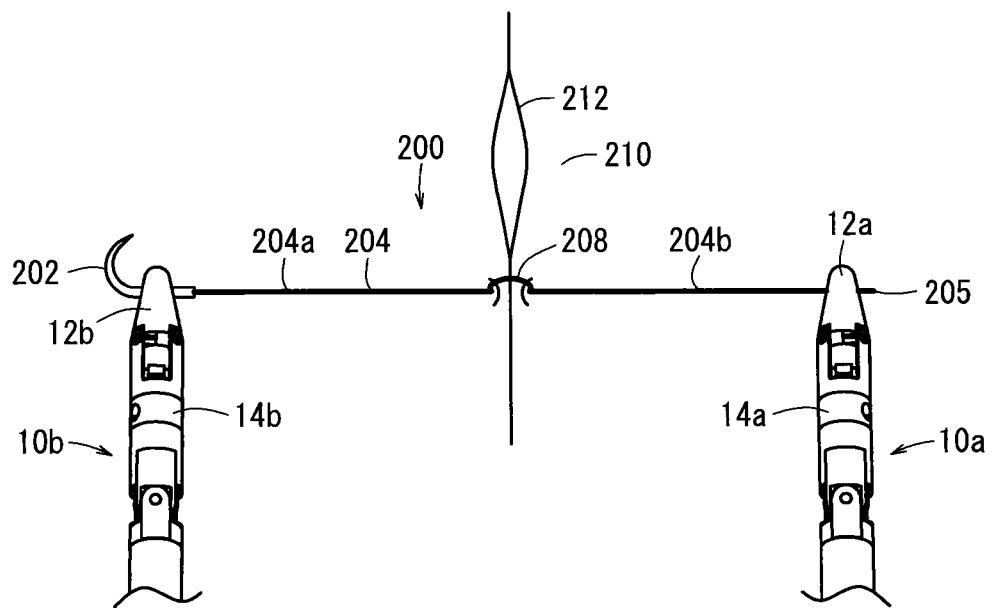
FIG. 15 is an eighth view illustrative of the intracoelomic ligating method.

The intracoelomic suturing and ligating method according to the present embodiment has a succession of steps including a needle piercing step (FIG. 8), a needle gripping step (FIG. 9), a winding step (FIGS. 10, 11), a transferring step (FIG. 12), a suture strand gripping step (FIG. 13), a pulling step (FIG. 14), and a tightening step (FIG. 15). These steps will be described below.

Figure 8:
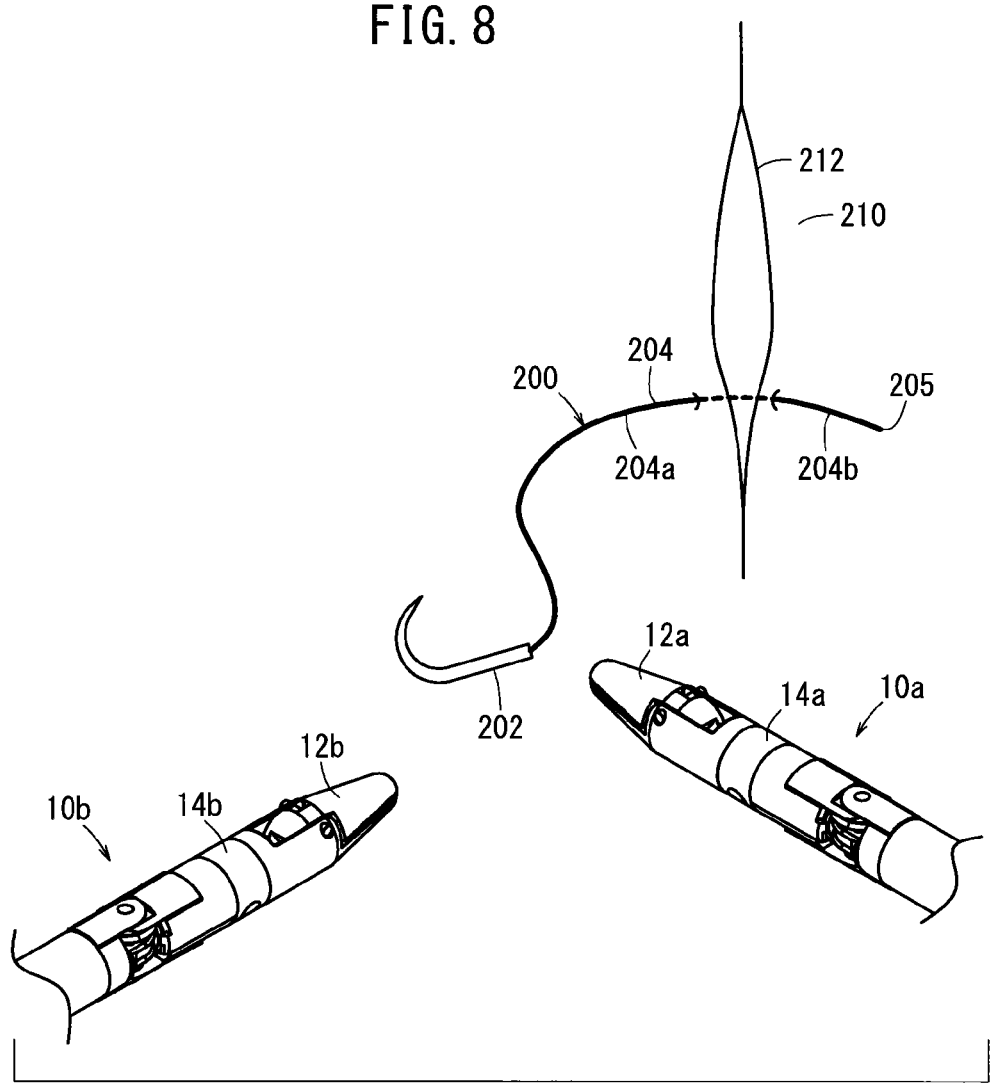
FIG. 8 is a first view illustrative of an intracoelomic ligating method.

As shown in FIG. 8, a suture-needle assembly 200 brought into a body cavity of the patient includes a needle 202 and a suture strand 204 connected to the proximal end of the needle 202. In the needle piercing step, the needle 202 is inserted through a tissue 210 in the body cavity, leaving a portion of the suture strand 204 uninserted in the tissue 210. Specifically, the needle 202 is inserted through the tissue 210 (a region to be treated) with an incision 212 being formed thereon in the body cavity, and an intermediate portion of the suture strand 204 is positioned in the tissue 210 and an end portion 205 is left uninserted in the tissue 210. A portion of the suture strand 204 that has passed (penetrated) through the tissue 210 in the needle piercing step, i.e., a portion of the suture strand 204 that extends between the needle 202 and the tissue 210, is referred to as "a passed portion 204*a*", and a portion of the suture strand 204 that has not passed through the tissue 210 in the needle piercing step, i.e., a portion of the suture strand 204 located on one side of the tissue 210 remote from the needle 202, is referred to as "an unpassed portion 204*b*". The unpassed portion 204*b* includes an end portion 205 of the suture strand 204 remote from the needle 202.

According to the present embodiment, the needle 202 comprises a curved needle which is substantially J-shaped. Though the needle 202 may be a straight needle, it should preferably be a curved needle, and the use of such a curved needle facilitates the needle piercing step as a surgical technique.

The user carries out the surgical technique of the needle piercing step using the first manipulator 10*a* or the second manipulator 10*b* alone or both the first manipulator 10*a* and the second manipulator 10*b* in combination. The user may alternatively perform the needle piercing step using a conventional needle driver. Since the surgical technique of the needle piercing step has heretofore been practiced in the art, details thereof will not be described.

Figure 9:
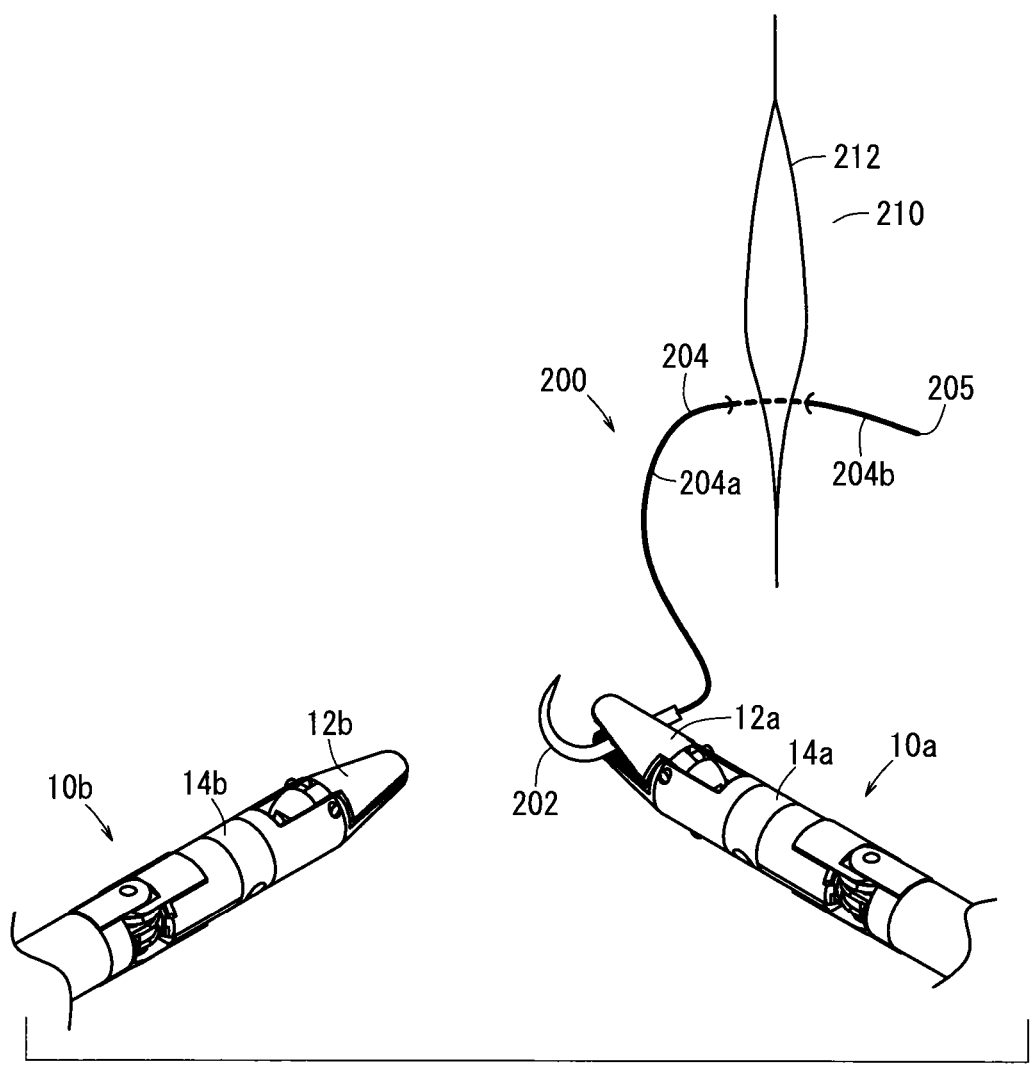
FIG. 9 is a second view illustrative of the intracoelomic ligating method.

In the needle gripping step, as shown in FIG. 9, the user grips the needle 202 with the first gripper 12*a* of the first manipulator 10*a*. If the user still holds the needle 202 with the first gripper 12*a* of the first manipulator 10*a* at the time the user has inserted an intermediate portion of the suture strand 204 into the incision 212 using the first manipulator 10*a* in the needle piercing step, then the user can carry out the needle gripping step by keeping gripping the needle 202 with the first gripper 12*a*.

Figure 10:
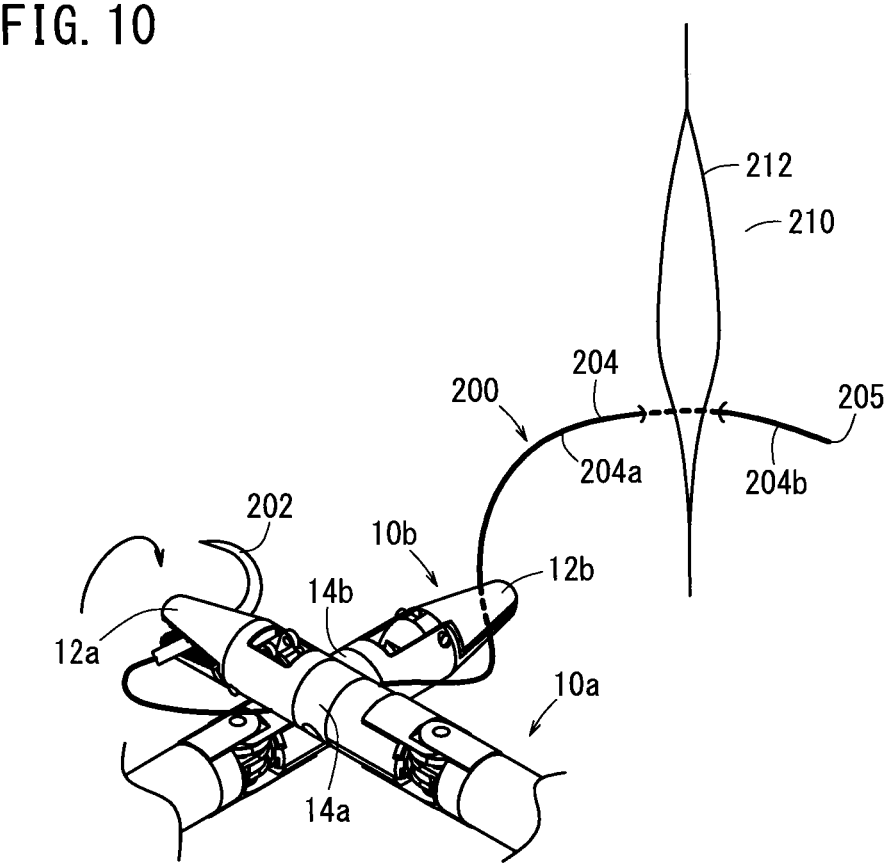
FIG. 10 is a third view illustrative of the intracoelomic ligating method.
Figure 11:
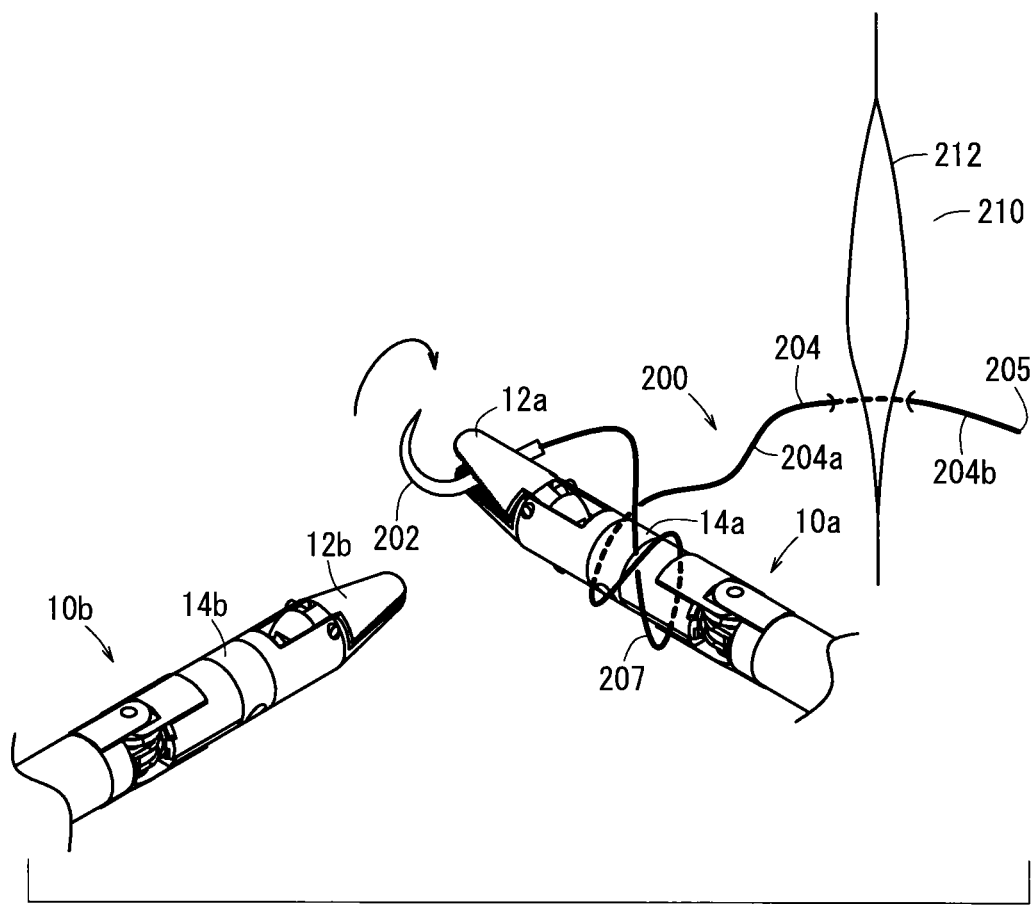
FIG. 11 is a fourth view illustrative of the intracoelomic ligating method.

The needle gripping step is followed by the winding step. In the winding step, as shown in FIGS. 10 and 11, the user rolls the first distal-end working unit 14*a* in one revolution or more while gripping the needle 202 with the first gripper 12*a*, thereby winding the suture strand 204 in one turn or more around the first distal-end working unit 14*a*. At this time, the user of the first manipulator 10*a* presses the rolling switch 28 (see FIG. 1) on the handle 16 thereof to cause the first distal-end working unit 14*a* to make a rolling movement.

Specifically, as shown in FIG. 10, the user starts to turn the first gripper 12*a* about its roll axis. In FIG. 10, the user rolls the first gripper 12*a* clockwise about the roll axis as viewed from the user. At the same time, the user uses the second manipulator 10*b* to displace the suture strand 204 from the first gripper 12*a* onto the first distal-end working unit 14*a* toward the proximal end of the first manipulator 10*a*. Specifically, the user pushes the passed portion 204*a* of the suture strand 204 with the second gripper 12*b* or a portion of the second distal-end working unit 14*b* other than the second gripper 12*b*, displacing the suture strand 204 axially to a position on the first distal-end working unit 14*a*. The suture strand 204 thus displaced onto the first distal-end working unit 14*a* can easily be wound around the first distal-end working unit 14*a*.

The user keeps rolling the first distal-end working unit 14*a* until the suture strand 204 is wound in one turn or more around the first distal-end working unit 14*a*, as shown in FIG. 11. In FIG. 11, the first distal-end working unit 14*a* is shown as having made about two revolutions clockwise from the state shown in FIG. 9, making about two turns of the suture strand 204 around the first distal-end working unit 14*a* thereby to produce a loop 207 of the suture strand 204 there-around. Depending on the nature of the tissue 210 or the endoscopic surgical operation on the patient, the suture strand 204 may be wound in one turn or three or more turns around the first distal-end working unit 14*a*. At the end of the winding step, the end portion 205 of the suture strand 204 has not passed through the tissue 210, but remains outside the tissue 210 on one side thereof remote from the needle 202.

Figure 12:
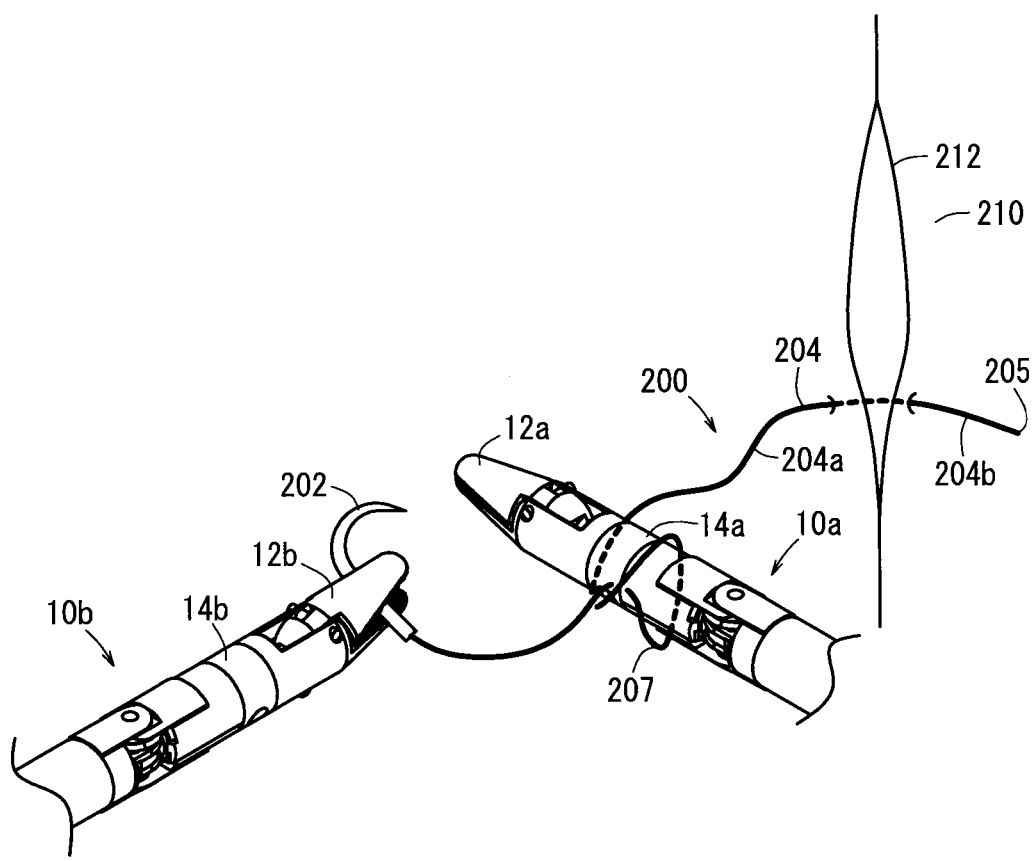
FIG. 12 is a fifth view illustrative of the intracoelomic ligating method.

After the winding step, the transferring step is carried out. In the transferring step, as shown in FIG. 12, the user transfers the suture-needle assembly 200 from the first gripper 12*a* of the first manipulator 10*a* to the second gripper 12*b* of the second manipulator 10*b*. Specifically, the user controls the second gripper 12*b* to grip the needle 202 which has been gripped by the first gripper 12*a*, and then opens the first gripper 12*a* to let the second gripper 12*b* to take over the needle 202 from the first gripper 12*a*. At the end of the transferring step, the end portion 205 of the suture strand 204 has not passed through the tissue 210, but remains outside the tissue 210 on one side thereof remote from the needle 202.

Figure 13:
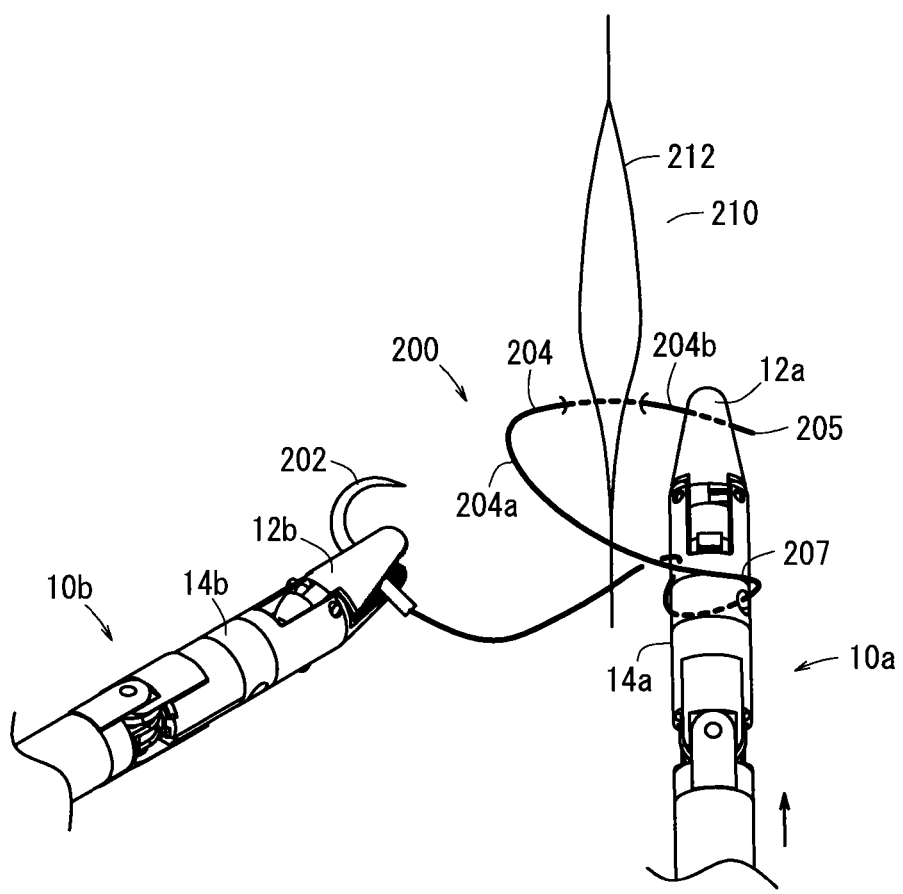
FIG. 13 is a sixth view illustrative of the intracoelomic ligating method.

Then, the user performs the suture strand gripping step after the transferring step. In the suture strand gripping step, as shown in FIG. 13, the user grips the unpassed portion 204*b* of the suture strand 204 with the first gripper 12*a* of the first manipulator 10*a*. Specifically, the user controls the first gripper 12*a* to grip the unpassed portion 204*b* of the suture strand 204. To grip the unpassed portion 204*b*, the user may appropriately adjust the angle and/or position of the first manipulator 10*a* with respect to the patient to move the first distal-end working unit 14*a* toward a portion of the suture strand 204 to be gripped by the first gripper 12*a*.

The pulling step is then carried out after the suture strand gripping step. In the pulling step, as shown in FIG. 14, the user pulls the first distal-end working unit 14*a* out of the loop 207 of the suture strand 204 wound around the first distal-end working unit 14*a*. Specifically, the user moves the first manipulator 10*a* in a direction toward the proximal end thereof, i.e., pulls the first manipulator 10*a* toward the user, allowing the loop 207 of the suture strand 204 wound around the first distal-end working unit 14*a* to slide with respect to the first distal-end working unit 14*a* toward the distal end thereof until the first distal-end working unit 14*a* pulls out of the loop 207. At this time, the unpassed portion 204*b* of the suture strand 204 gripped by the first gripper 12*a* passes through the loop 207.

The pulling step is followed by the tightening step. In the tightening step, as shown in FIG. 15, the user moves the first distal-end working unit 14*a* of the first manipulator 10*a* and the second distal-end working unit 14*b* of the second manipulator 10*b* away from each other, thereby forming a knot 208. Specifically, while gripping the suture strand 204 and the needle 202 with the first gripper 12*a* and the second gripper 12*b*, respectively, the user moves the first gripper 12*a* and the second gripper 12*b* in mutually opposite directions with the tissue 210 penetrated by the suture strand 204 being regarded as the center, tying the suture strand 204 into the knot 208 across the incision 212. In FIG. 15, the user has moved the first manipulator 10*a* to the right and the second manipulator 10*b* to the left as viewed from the user.

In the tightening step, the user may operate the first manipulator 10*a* and the second manipulator 10*b* to change their gripping positions of the suture strand 204 closer to the incision 212. If the gripping positions are closer to the incision 212, the user does not need to space the first distal-end working unit 14*a* and the second distal-end working unit 14*b* excessively away from each other, and finds it easy to perform surgical techniques in a small space in the body cavity. In the tightening step, the user may pull the suture strand 204 by tilting the distal-end working unit 14 of one or both of the first manipulator 10*a* and the second manipulator 10*b*.

After the tightening step shown in FIG. 15, the user may carry out the needle gripping step, the winding step, the transferring step, the suture strand gripping step, the pulling step, and the tightening step may be repeated at least once to strengthen the knot 208. Depending on the size (length) of the incision 212, a plurality of knots 208 may be formed at space intervals along the lengthwise direction of the incision 212.

With the intracoelomic suturing and ligating method according to the present embodiment, as described above, since the first distal-end working unit 14*a* can be rolled in an unlimited angular range, the user can wind the suture strand 204 easily in one turn or more around the first distal-end working unit 14*a* by controlling the first gripper 12*a* thereof to make one revolution or more while gripping the needle 202 with the first gripper 12*a*. In thus winding the suture strand 204 around the first distal-end working unit 14*a*, the first manipulator 10*a* only operates to roll the first distal-end working unit 14*a* and does not move in the body cavity. Therefore, the user finds the first manipulator 10*a* suitable for surgical techniques in a small space in the body cavity.

The intracoelomic suturing and ligating method makes it possible to suture and ligate the tissue 210 in the body cavity more easily than suturing and ligating methods according to the related art using a needle driver. Some needle drivers according to the related art which are manually operated may be rolled in an unlimited angular range. However, in order for such needle drives to be rolled through an angular range of 360° or greater, the user needs to manually turn a rolling handle many times. The needle drivers according to the related art thus fail to perform the surgical technique of the winding step as simply as the intracoelomic suturing and ligating method according to the present invention.

If a medical manipulator having a motor for making a rolling movement, as disclosed in U.S. Patent Application Publication No. 2009/0240263, for example, is used, then since the medical manipulator rolls the gripper based on the drive force transmitted from the motor through pulleys, wires, etc., the rolling movement is limited to an angular range of less than 360°. Because of the limited angular range for the rolling movement, the disclosed medical manipulator is unable to perform the winding step of the intracoelomic suturing and ligating method according to the present invention.

On the other hand, with the intracoelomic suturing and ligating method according to the present embodiment, the first manipulator 10*a* allows the first distal-end working unit 14*a* to roll in an unlimited angular range based on the drive force generated from the motor 38 which is energized when the rolling switch 28 (see FIG. 1) is turned on. Thus, the user can control the first manipulator 10*a* to reliably wind the suture strand 204 around the first distal-end working unit 14*a* simply by pressing the rolling switch 28 on the handle 16. The intracoelomic suturing and ligating method can, therefore, suture and ligate the tissue 210 more easily.

With the intracoelomic suturing and ligating method according to the present embodiment, furthermore, the first manipulator 10*a* rolls the first distal-end working unit 14*a* while the second manipulator 10*b* has displaced the suture strand 204 toward the first distal-end working unit 14*a* in the winding step (see FIG. 10). Consequently, the suture strand 204 can easily be wound around the first distal-end working unit 14a. The user can thus perform the surgical technique of winding the suture strand quickly and reliably.

In the above embodiment, each of the first manipulator 10a and the second manipulator 10b is constructed as the manipulator 10 having the distal-end working unit 14 with multiple degrees of freedom and the motor 38 for rolling the distal-end working unit 14 about the roll axis. According to a modification, the second manipulator 10b may be replaced with general forceps (laparoscopic forceps) free of a drive source.

The intracoelomic suturing and ligating method according to the above embodiment is applied to suturing and ligating surgical techniques. However, it is also applicable to a ligating treatment for a fissure or vessel, e.g., DVC (Dorsal Vein Complex) ligation in prostatectomy.

Although a certain preferred embodiment of the present invention has been shown and described in detail, it should be understood that various changes and modifications may be made therein without departing from the scope of the appended claims.

What is claimed is:

1. A suturing and ligating method to be performed inside a body cavity, the method comprising:

a using step of using a first manipulator having a first distal-end working unit including a first gripper which is selectively openable and closable, the first distal-end working unit being configured to make a rolling movement without rotating the first manipulator as a whole, and a second manipulator having a second distal-end working unit including a second gripper which is selectively openable and closable, the first manipulator including a handle having a rolling operating unit, a shaft extending from the handle, the first distal-end working unit mounted on a distal end of the shaft, and a drive source removably mounted in the handle to roll the first distal-end working unit in an unlimited angular range around a longitudinal axis of the first distal-end working unit via an automated motion, the drive source being energized when the rolling operating unit is operated, a needle piercing step of inserting a needle of a suture-needle assembly through a tissue in the body cavity while leaving a portion of a suture strand of the suture-needle assembly uninserted in the tissue;

a needle gripping step of gripping the needle with the first gripper;

a winding step of winding the suture strand in at least one turn around the first distal-end working unit by energizing the drive source to roll the first distal-end working unit in at least one revolution via the automated motion around the longitudinal axis while gripping the needle with the first gripper;

a transferring step of, after the winding step, transferring the suture-needle assembly from the first gripper to the second gripper;

a suture strand gripping step of, after the transferring step, gripping a portion of the suture strand that has not passed through the tissue, with the first gripper;

a pulling step of, after the suture strand gripping step, pulling the first distal-end working unit out of a loop of the suture strand wound around the first distal-end working unit; and a tightening step of, after the pulling step, forming a knot of the suture strand by moving the first distal-end working unit and the second distal-end working unit away from each other.

2. The method according to claim 1, wherein the winding step comprises rolling the first distal-end working unit while displacing the suture strand toward the first distal-end working unit by the second manipulator.

* * * * *